US011913055B2

(12) United States Patent
Chen et al.

(10) Patent No.: US 11,913,055 B2
(45) Date of Patent: Feb. 27, 2024

(54) CONTINUOUS FLOW METHOD FOR PREPARING (R)-3-HYDROXY-5-HEXENOATE

(71) Applicant: Fudan University, Shanghai (CN)

(72) Inventors: Fener Chen, Shanghai (CN); Dang Cheng, Shanghai (CN); Zedu Huang, Shanghai (CN); Chen Hu, Shanghai (CN); Meifen Jiang, Shanghai (CN); Minjie Liu, Shanghai (CN); Huashan Huang, Shanghai (CN)

(73) Assignee: Fudan University, Shanghai (CN)

( * ) Notice: Subject to any disclaimer, the term of this patent is extended or adjusted under 35 U.S.C. 154(b) by 154 days.

(21) Appl. No.: 17/504,858

(22) Filed: Oct. 19, 2021

(65) Prior Publication Data

US 2022/0033863 A1 Feb. 3, 2022

(30) Foreign Application Priority Data

Oct. 22, 2020 (CN) .......................... 202011136206.9

(51) Int. Cl.
| | | |
|---|---|---|
| C12P 7/42 | (2006.01) | |
| C12P 7/62 | (2022.01) | |
| C12N 9/04 | (2006.01) | |
| C12M 3/06 | (2006.01) | |
| C12N 11/084 | (2020.01) | |
| C12N 11/089 | (2020.01) | |
| C12M 1/40 | (2006.01) | |
| C12M 1/00 | (2006.01) | |

(52) U.S. Cl.
CPC ............... *C12P 7/62* (2013.01); *C12M 21/18* (2013.01); *C12M 23/16* (2013.01); *C12M 29/00* (2013.01); *C12N 11/084* (2020.01); *C12N 11/089* (2020.01); *C12Y 101/0108* (2013.01); *C12Y 101/01184* (2013.01)

(58) Field of Classification Search
CPC . C12P 7/62; C12P 7/42; C12P 41/002; C12M 21/18; C12M 23/16; C12M 29/00; C12M 23/08; C12M 37/04; C12M 41/22; C12N 11/084; C12N 11/089; C12N 9/0006; C12Y 101/0108; C12Y 101/01184; Y02P 20/50

See application file for complete search history.

(56) References Cited

U.S. PATENT DOCUMENTS

| | | | |
|---|---|---|---|
| 6,355,822 B1 | 3/2002 | Johnson et al. | |
| 10,526,622 B2 | 1/2020 | Chen et al. | |
| 2018/0340196 A1* | 11/2018 | Chen et al. | ............... C12P 7/62 |

FOREIGN PATENT DOCUMENTS

| | | |
|---|---|---|
| CN | 101735272 B | 10/2012 |
| CN | 107119081 A | 9/2017 |
| CN | 108359626 A | 8/2018 |
| CN | 111686809 A | 9/2020 |
| EP | 1176135 B1 | 6/2005 |
| WO | 03053950 A1 | 7/2003 |
| WO | 2016074324 A1 | 5/2016 |

OTHER PUBLICATIONS

Bennett et al., Methyl (3R)-3-hydroxyhex-5-enoate as a precursor to chiral mevinic acid analogues[J].Journal of the Chemical Society, Perkin Transactions 1, 1991, 133-140.

Huang et al., Chiral syn-1,3-diol derivatives via a one-pot diastereoselective carboxylation/ bromocyclization of homoallylic alcohols[J]. iScience, 2018, 513-520.

* cited by examiner

*Primary Examiner* — Satyendra K Singh

(57) ABSTRACT

Disclosed herein relates to biopharmaceuticals, and more particularly to a continuous flow method for preparing (R)-3-hydroxy-5-hexenoate. Carbonyl reductase and isopropanol dehydrogenase are co-immobilized onto an inert solid medium simultaneously to prepare a carbonyl reductase/isopropanol dehydrogenase co-immobilized catalyst, which is then filled into a microchannel reactor of the micro reaction system. A solution containing substrate 3-carbonyl-5-hexenoate is subsequently pumped into the microchannel reactor to perform an asymmetric carbonyl reduction reaction to obtain (R)-3-hydroxy-5-hexenoate.

12 Claims, 1 Drawing Sheet

Specification includes a Sequence Listing.

SEQUENCE LISTING

<160> NUMBER OF SEQ ID NOS: 2

<210> SEQ ID NO 1
<211> LENGTH: 252
<212> TYPE: PRT
<213> ORGANISM: Artificial Sequence
<220> FEATURE:
<223> OTHER INFORMATION: synthetic

<400> SEQUENCE: 1

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
                20                  25                  30

Lys Val Val Ile Thr Gly Arg Arg Ala Asp Val Gly Glu Arg Ala Ala
            35                  40                  45

Lys Ser Ile Gly Gly Thr Asp Val Ile Arg Phe Ile Gln His Asp Ala
        50                  55                  60

Ser Asp Glu Ala Gly Trp Thr Lys Leu Phe Asp Thr Thr Glu Glu Ala
65                  70                  75                  80

Phe Gly Pro Val Thr Thr Val Asn Asn Ala Gly Ile Asp Val Val
                85                  90                  95

Lys Ser Val Glu Asp Thr Thr Thr Glu Glu Trp His Lys Leu Leu Ser
                100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Ile
    130                 135                 140

Phe Gly Met Val Gly Asp Pro Thr Val Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Val Glu Gly Ala Glu Met Trp Ser Gln
        195                 200                 205

Arg Thr Lys Thr Pro Met Gly His Ile Gly Pro Asn Asp Ile Ala
    210                 215                 220

Trp Val Cys Val Tyr Leu Ala Ser Gly Glu Ser Lys Phe Ala Thr Gly
225                 230                 235                 240

Ala Glu Phe Val Ile Asp Gly Gly Trp Thr Ala Gln
                245                 250
```

<210> SEQ ID NO 2
<211> LENGTH: 252
<212> TYPE: PRT
<213> ORGANISM: Artificial Sequence
<220> FEATURE:
<223> OTHER INFORMATION: synthetic

<400> SEQUENCE: 2

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
                20                  25                  30

Lys Val Val Ile Thr Gly Arg His Ala Asp Val Gly Glu Lys Ala Ala
            35                  40                  45
```

```
Lys Ser Ile Gly Gly Thr Asp Val Ile Arg Phe Val Gln His Asp Ala
    50              55                  60

Ser Asp Glu Ala Gly Trp Thr Lys Leu Phe Asp Thr Thr Glu Glu Ala
65              70                  75                      80

Phe Gly Pro Val Thr Thr Val Val Asn Asn Ala Gly Ile Ala Val Ser
                85              90                      95

Lys Ser Val Glu Asp Thr Thr Thr Glu Glu Trp Arg Lys Leu Leu Ser
                100             105                 110

Val Asn Leu Asp Gly Val Phe Phe Gly Thr Arg Leu Gly Ile Gln Arg
            115             120                 125

Met Lys Asn Lys Gly Leu Gly Ala Ser Ile Ile Asn Met Ser Ser Ile
        130             135             140

Glu Gly Phe Val Gly Asp Pro Thr Leu Gly Ala Tyr Asn Ala Ser Lys
145             150             155                     160

Gly Ala Val Arg Ile Met Ser Lys Ser Ala Ala Leu Asp Cys Ala Leu
                165             170                 175

Lys Asp Tyr Asp Val Arg Val Asn Thr Val His Pro Gly Tyr Ile Lys
            180             185                 190

Thr Pro Leu Val Asp Asp Leu Glu Gly Ala Glu Glu Met Met Ser Gln
        195             200                 205

Arg Thr Lys Thr Pro Met Gly His Ile Gly Glu Pro Asn Asp Ile Ala
    210             215             220

Trp Ile Cys Val Tyr Leu Ala Ser Asp Glu Ser Lys Phe Ala Thr Gly
225             230             235                     240

Ala Glu Phe Val Val Asp Gly Gly Tyr Thr Ala Gln
                245             250
```

CONTINUOUS FLOW METHOD FOR PREPARING (R)-3-HYDROXY-5-HEXENOATE

REFERENCE TO AN ELECTRONIC SEQUENCE LISTING

The contents of the electronic sequence listing (SequenceListing-20231211.txt; Size: 4,808 bytes; and Date of Creation: Dec. 12, 2023) is herein incorporated by reference in its entirety.

CROSS-REFERENCE TO RELATED APPLICATIONS

This application claims the benefit of priority from Chinese Patent Application No. 202011136206.9, filed on Oct. 22, 2020. The content of the aforementioned application, including any intervening amendments thereto, is incorporated herein by 15 reference in its entirety.

TECHNICAL FIELD

This disclosure relates to biopharmaceuticals, and more particularly to a continuous flow method for preparing (R)-3-hydroxy-5-hexenoate.

BACKGROUND (R)-3-hydroxy-5-hexenoate has a structure of formula (I):

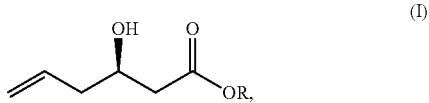

(I)

where R is linear or branched $C_1$-$C_8$ alkyl group, linear or branched $C_3$-$C_8$ cycloalkyl group, monosubstituted or polysubstituted aryl group, or monosubstituted or polysubstituted aralkyl group. The compound (I) is a key chiral intermediate for the preparation of a variety of drugs such as atorvastatin, rosuvastatin, pitavastatin and fluvastatin (World patent Nos. 2016074324 and 2003053950; Chinese patent No. 101735272; Bennett et al., Methyl (3R)-3-hydroxyhex-5-enoate as a precursor to chiral mevinic acid analogues[J]. *Journal of the Chemical Society, Perkin Transactions* 1, 1991, 133-140; Huang et al., Chiral syn-1,3-diol derivatives via a one-pot diastereoselective carboxylation/bromocyclization of homoallylic alcohols[J]. *iScience*, 2018, 513-520).

As disclosed by U.S. Pat. No. 6,355,822, sodium borohydride was reacted with tartaric acid in situ to give a chiral reducing agent, which was then employed tostereoselectively reduce 3-carbonyl-5-hexenoate to obtain the compound (I). However, this method required low-temperature reaction conditions (−20° C. to −50° C.), which led to high energy consumption and cost, limiting its practical application. EP patent No. 1176135 disclosed a process for preparing the compound (I) by using the asymmetric catalytic hydrogenation of 3-carbonyl-5-hexenoate with a complex of ruthenium and a chiral phosphine ligand, which was not applicable to the industrial production due to the drawbacks of harsh reaction conditions (high temperature and high pressure), complicated operation, high safety risks and significant scale-up effect. Interestingly, a baker's yeast was adopted by Bennett et al. (Methyl (3R)-3-hydroxyhex-5-enoate as a precursor to chiral mevinic acid analogues[J]. *Journal of the Chemical Society, Perkin Transactions* 1, 1991, 133-140) to biologically catalyze the reduction of 3-carbonyl-5-hexenoate to access the compound (I). Compared to the above methods, this method had mild reaction conditions, but it suffered from poor stereoselectivity (only 43-78% ee (enantiomeric excess)). Chinese patent application publication Nos. 107119081A and 108359626A and U.S. patent Ser. No. 10/526,622 disclosed a method for preparing the compound (I) by reducing 3-carbonyl-5-hexenoate using carbonyl reductase and isopropanol dehydrogenase. This method had mild reaction conditions and high optical purity (greater than 99% ee), but it was greatly limited by the long reaction times (more than 10 h) and low yields. These enzymatic methods are all performed using a crude enzyme solution, in which the free-state enzyme had poor stability and was prone to inactivation. Moreover, these methods also suffered from complicated workup procedures, difficult recovery of the enzyme and high cost. Chinese patent application publication No. 111686809A disclosed a method for preparing the compound (I) using a co-supported biocatalyst. It appeared that the enzyme stability was improved and enzyme recovery was facilitated, but this method still suffered from long reaction times and low yields.

These enzymatic methods are all carried out in traditional batch reactors, which are limited by their poor multiphase mass transfer and mixing performances, decreasing reaction rate and selectivity. As a consequence, the traditional enzymatic methods suffer from long reaction times, low efficiencies and low yields. Moreover, it is very difficult or even impossible to recover the free-state enzyme, while additional complex procedures (e.g., shutdown process, filtration, re-start-up process etc.) are required to recover the supported enzyme, which considerably lowers the production efficiency and increases the process cost.

So far, the continuous flow synthesis of (R)-3-hydroxy-5-hexenoate (I) based on the enzymatic asymmetric reduction of 3-carbonyl-5-hexenoate (II) has not been reported in the literature. In view of this, there is an urgent need for those skilled in the art to develop a rapid, operationally simple, high-yielding and efficient method for continuously preparing (R)-3-hydroxy-5-hexenoate with a high degree of automation to overcome the defects in the existing enzymatic methods.

SUMMARY

An object of this disclosure is to provide a continuous flow method for preparing (R)-3-hydroxy-5-hexenoate to overcome the drawbacks of the prior art. The method provided herein leads to very short reaction time, improved efficiency and much increased yield of (R)-3-hydroxy-5-hexenoate, simplified operation and a higher degree of automation, and thus it is very promising for industrial applications.

Technical solutions of this disclosure are described as follows.

In a first aspect, this disclosure provides a continuous flow method for preparing (R)-3-hydroxy-5-hexenoate using a micro reaction system, wherein the micro reaction system comprises a microchannel reactor, and the method comprises:

(1) Co-immobilizing carbonyl reductase and isopropanol dehydrogenase onto an inert solid medium simultaneously to prepare a co-immobilized catalyst; and filling the microchannel reactor with the co-immobilized catalyst;

(2) pumping a substrate solution containing a 3-carbonyl-5-hexenoate into the microchannel reactor to perform an asymmetric carbonyl reduction reaction; and (3) collecting the reaction mixture flowing out of the microchannel reactor followed by separation and purification to obtain a target product (R)-3-hydroxy-5-hexenoate;

wherein the (R)-3-hydroxy-5-hexenoate is shown in formula (I), and the 3-carbonyl-5-hexenoate is shown in formula (II); and the asymmetric carbonyl reduction reaction is shown in the following reaction scheme:

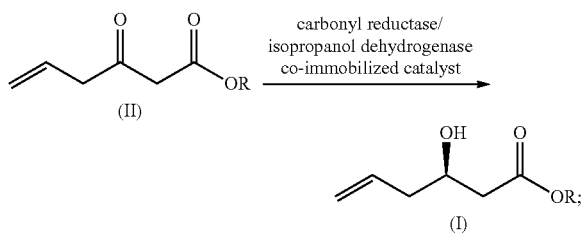

wherein R is linear or branched $C_1$-$C_8$ alkyl group, linear or branched $C_3$-$C_8$ cycloalkyl group, monosubstituted or polysubstituted aryl group, or monosubstituted or polysubstituted aralkyl group.

In some embodiments, in step (1), the inert solid medium is a composite material of polyvinyl alcohol and polyethylene glycol; and the step of "co-immobilizing carbonyl reductase and isopropanol dehydrogenase onto an inert solid medium simultaneously to prepare the co-immobilized catalyst" comprises:

(a) preparing an aqueous solution of the polyvinyl alcohol and the polyethylene glycol; heating the aqueous solution until the aqueous solution becomes clear; and cooling the aqueous solution to 50° C. or less to obtain a first solution;

(b) adding a crude carbonyl reductase solution and a crude isopropanol dehydrogenase solution into the first solution followed by uniform mixing to obtain a second solution; and (c) dropwise adding the second solution onto a polyethylene film; drying the polyethylene film at 35-40° C. for 0.5-1 h to obtain the co-immobilized catalyst; and storing the co-immobilized catalyst at 4° C. for later use.

In some embodiments, an amino acid sequence of the carbonyl reductase is shown in SEQ ID NO: 1, and an amino acid sequence of the isopropanol dehydrogenase is shown in SEQ ID NO: 2.

In some embodiments, a weight ratio of the polyvinyl alcohol to the polyethylene glycol is 5:1-3.

In some embodiments, the crude carbonyl reductase solution and the crude isopropanol dehydrogenase solution both have an initial concentration of 10%-30% (w/v).

In some embodiments, in step (b), a volume ratio of the crude carbonyl reductase solution to the crude isopropanol dehydrogenase solution to the first solution is 2:1:5-10.

In some embodiments, the microchannel reactor is a tubular microchannel reactor or a plate-type microchannel reactor.

In some embodiments, the microchannel reactor is a tubular microchannel reactor with an inner diameter of 100 μm-20 mm, preferably 120 μm-10 mm.

In some embodiments, the microchannel reactor is a plate-type microchannel reactor having a reaction fluid channel with a hydraulic diameter of 100 μm-20 mm, preferably 120 μm-10 mm.

In some embodiments, in step (2), the substrate solution is prepared by dissolving 3-carbonyl-5-hexenoate (II), isopropanol, coenzyme $NADP^+$ and an organic solvent in a phosphate buffered solution (PBS).

In some embodiments, the organic solvent is a polar aprotic solvent; the organic solvent is N,N-dimethylformamide, dimethyl sulfoxide, N-methylpyrrolidone, sulfolane, 1,3-dimethyl-2-imidazolinone, hexamethylphosphoric triamide, acetonitrile and a ketone solvent.

In some embodiments, the substrate solution comprises 1-100 g/L of 3-carbonyl-5-hexenoate (II), 1-50 g/L of isopropanol, 0.005-0.1 g/L of the coenzyme $NADP^+$ and 20-250 g/L of the organic solvent.

In some embodiments, the phosphate buffered solution is an aqueous solution of a mixture of disodium hydrogen phosphate and sodium dihydrogen phosphate or potassium dihydrogen phosphate.

In some embodiments, the phosphate buffered solution has a pH of 6-8, preferably 6.5-7.5.

In some embodiments, in step (2), the asymmetric carbonyl reduction reaction is performed at 15-40° C., preferably 20-35° C.; and a residence time of the substrate solution in the microchannel reactor is 0.1-30 min.

In some embodiments, the micro reaction system further comprises a feeding pump and a back pressure regulator; an inlet of the microchannel reactor is connected to the feeding pump, and an outlet of the microchannel reactor is connected to the back pressure regulator; and a back pressure range of the back pressure regulator is 0.1-3 MPa.

In some embodiments, the step (3) specifically comprises:
collecting the reaction mixture flowing out of the micro reaction system;
subjecting the reaction mixture to extraction with ethyl acetate 3 times;
collecting and combining organic phases; washing the combined organic phase sequentially with water and saturated brine; and
drying the combined organic phase with anhydrous sodium sulfate followed by vacuum concentration to obtain a target product (R)-3-hydroxy-5-hexenoate.

In a second aspect, this disclosure provides a micro reaction system for continuously preparing (R)-3-hydroxy-5-hexenoate, comprising:
a feeding pump;
a microchannel reactor; and
a back pressure regulator;
wherein an inlet of the microchannel reactor is connected to the feeding pump, and an outlet of the microchannel reactor is connected to the back pressure regulator;
the microchannel reactor is filled with a carbonyl reductase/isopropanol dehydrogenase co-immobilized catalyst, and the carbonyl reductase/isopropanol dehydrogenase co-immobilized catalyst is prepared by co-immobilizing carbonyl reductase and isopropanol dehydrogenase onto an inert solid medium simultaneously;
the feeding pump is configured to pump a substrate solution containing 3-carbonyl-5-hexenoate into the microchannel reactor to perform an asymmetric carbonyl reduction reaction; and the back pressure regulator is configured to provide a pressure to the microchannel reactor; and the reaction mixture is discharged from the back pressure regulator to afford a target product (R)-3-hydroxy-5-hexenoate;

wherein the (R)-3-hydroxy-5-hexenoate is shown in formula (I):

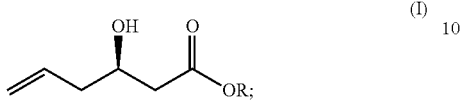

the 3-carbonyl-5-hexenoate is shown in formula (II):

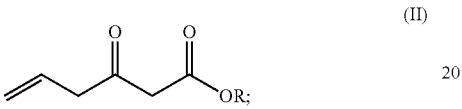

wherein R is linear or branched $C_1$-$C_8$ alkyl group, linear or branched $C_3$-$C_8$ cycloalkyl group, monosubstituted or polysubstituted aryl group, or monosubstituted or polysubstituted aralkyl group.

In some embodiments, the microchannel reactor is a tubular microchannel reactor or a plate-type microchannel reactor.

In some embodiments, the microchannel reactor is further sequentially connected to a microfluidic liquid-liquid extractor and a liquid-liquid membrane separator to achieve continuous enzymatic reaction, liquid-liquid extraction and separation.

In some embodiments, the microchannel reactor is further connected to a multi-stage extraction and separation unit to achieve continuous enzymatic reaction, liquid-liquid extraction and separation. The multi-stage extraction and separation unit is composed of at least two pairs of microfluidic liquid-liquid extractor and liquid-liquid membrane separator that are sequentially connected in series. For example, a two-stage extraction and separation unit comprises a first microfluidic liquid-liquid extractor, a first liquid-liquid membrane separator, a second microfluidic liquid-liquid extractor, and a second liquid-liquid membrane separator that are sequentially connected in series; a three-stage extraction and separation unit comprises a first microfluidic liquid-liquid extractor, a first liquid-liquid membrane separator, a second microfluidic liquid-liquid extractor, a second liquid-liquid membrane separator, a third microfluidic liquid-liquid extractor, and a third liquid-liquid membrane separator that are sequentially connected in series.

In some embodiments, the microchannel reactor is further connected to a centrifugal extractor or at least two centrifugal extractors installed in series to achieve continuous enzymatic reaction, liquid-liquid extraction and separation.

In some embodiments, at least two micro reaction systems are simultaneously operated in parallel under the same conditions for the same period of time to increase the productivity. Compared to the prior art, this disclosure has the following beneficial effects.

1) The microchannel system used herein has excellent mass transfer and molecular mixing performances, by which the reaction time of the enzymatic asymmetric reduction of 3-carbonyl-5-hexenoate is shortened from more than 10 h (in a traditional batch reactor) to just a few minutes. Moreover, the side reactions are largely suppressed by using the microchannel system, and the yield of (R)-3-hydroxy-5-hexenoate is increased from 80% to more than 95%. Several reasons have contributed to reduce the reaction time and increase the yield in flow. Firstly, the high efficiency of mixing and interphase mass transfer characteristics of the continuous flow reactor might have intensified this enzymatic reaction. Secondly, the plug flow pattern (i.e., no back-mixing) inside the flow reactor might be helpful to overcome the substrate/product inhibition phenomena. Thirdly, the higher ratio of local enzymes to substrate achieved in the flow reactor might also have contributed to shorten the reaction time and suppress the side reactions.

2) The asymmetric carbonyl reduction reaction of 3-carbonyl-5-hexenoate is enabled when the substrate solution flowing in the reaction fluid channel of the microchannel reactor that is filled with the carbonyl reductase/isopropanol dehydrogenase co-immobilized catalyst, allowing for continuous preparation without any external interventions, simple operation, a higher degree of automation, high time and space efficiency, and low labor intensity and production cost.

3) The continuous flow process based on the microchannel reactor does not require separation of the co-immobilized catalyst from the reaction mixture and, so that the reaction system can be operated continuously for a long time to greatly improve the efficiency, and the separation cost and the cost of catalyst recycling can be avoided.

4). The continuous flow method allows for easy integration of enzymatic reaction with continuous liquid-liquid extraction and separation units, eliminating the need for manual workup procedures including filtration, liquid-liquid extraction and separation, thereby reducing the processing time needed, minimizing the energy consumed and the waste generated. These workup procedures are unavoidable in batch-wise synthesis and incur additional costs. Additionally, continuous flow synthesis can be readily scaled up by using the numbering-up strategy, the productivity can thus be significantly increased by simultaneously operating multiple micro reaction systems in parallel under the same conditions for the same period of time.

Figure 1:
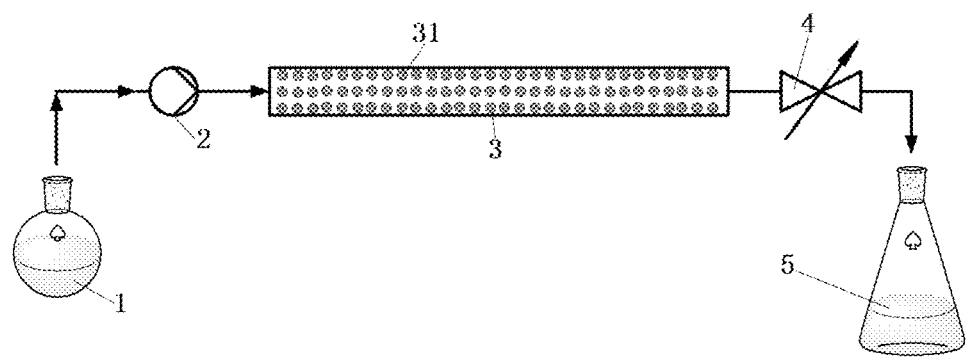
FIG. 1 is a schematic diagram of a micro reaction system in accordance with an embodiment of this disclosure.

In the drawings: 1, container; 2, feeding pump; 3, microchannel reactor; 31. carbonyl reductase/isopropanol dehydrogenase co-immobilized catalyst; 4, back pressure regulator; 5, collecting bottle; 6. plate-type microchannel reactor; 61, first temperature control layer; 62, second temperature control layer; and 63, reaction layer.

DETAILED DESCRIPTION OF EMBODIMENTS

In order to make the technical solutions, structural features, objectives and beneficial effects clear, this disclosure will be illustrated in detail below with reference to the embodiments. It should be noted that these embodiments are merely illustrative of the disclosure, and are not intended to limit the disclosure.

As used herein, term "alkyl" refers to a $C_1$-$C_8$ alkyl group, preferably $C_1$-$C_5$ alkyl group, linear or branched alkyl group, such as methyl, ethyl, n-propyl, isopropyl, n-butyl, isobutyl, sec-butyl, tert-butyl, n-pentyl and n-hexyl.

As used herein, term "$C_3$-$C_8$ cycloalkyl group" includes but is not limited to cyclopropyl, cyclobutyl, cyclopentyl and cyclohexyl.

As used herein, term "aryl" refers to a monocyclic, polycyclic or polycylic aromatic aryl group having 6 to 36 carbon atoms, preferably 6 to 14 carbon atoms, such as phenyl, naphthyl, anthryl, phenanthryl, biphenyl and binaphthyl. The aryl can be monosubstituted or polysubstituted, for example, the aryl can carry one or more substituents such as alkyl group.

As used herein, term "aralkyl" refers to an alkyl in which at least one hydrogen atom is substituted with an aryl, preferably an aralkyl with 7 to 15 carbon atoms, such as benzyl, 1-phenethyl, 2-phenethyl, 1-phenylpropyl, and 3-naphthylpropyl. The aryl in the aralkyl can be monosubstituted or polysubstituted. For example, the aryl in the aralkyl can have one or more substituents such as alkyl.

As used herein, an amino acid sequence of the carbonyl reductase is shown in SEQ ID NO: 1, and an amino acid sequence of the isopropanol dehydrogenase is shown in SEQ ID NO: 2.

Detailed description will be given below with reference to the embodiments. It should be noted that unless otherwise specified, the materials and reagents used below are all commercially available.

Example 1 Preparation of a Carbonyl Reductase/Isopropanol Dehydrogenase Co-Supported Catalyst 5 g of polyvinyl alcohol, 3 g of polyethylene glycol and 35 mL of water were added into a reaction flask and heated until the reaction mixture became clear. After cooled to 50° C. or less, the reaction mixture was added with 10 mL of a crude carbonyl reductase solution (15% w/v) and 5 mL of a crude isopropanol dehydrogenase solution (15% w/v) and mixed thoroughly. Then the reaction mixture was added dropwise to a polyethylene film using a syringe, and the polyethylene film was dried at 35° C. in a drying oven for 1 h to obtain a carbonyl reductase/isopropanol dehydrogenase co-immobilized catalyst which was stored at 4° C. for later use.

With regard to the preparation of the crude carbonyl reductase solution and the crude isopropanol dehydrogenase solution, methods mentioned in Chinese patent application publication No. 107119081A were incorporated herein by reference.

Example 2 Preparation of Target Product tert-butyl (R)-3-hydroxy-5-hexenoate

The micro reaction system shown in FIG. 1 was adopted herein, where the microchannel reactor 3 was a tubular microchannel reactor. 5 g of the carbonyl reductase/isopropanol dehydrogenase co-supported catalyst prepared in Example 1 was filled into the tubular microchannel reactor 3 with an inner diameter of 10 mm and a length of 200 mm. A disodium hydrogen phosphate-potassium dihydrogen phosphate buffered solution (pH 7.0) was first pumped into the tubular microchannel reactor 3 at a flow rate of 5 mL/min using a feeding pump 2 to wash the carbonyl reductase/isopropanol dehydrogenase co-supported catalyst 31 for 5 min. Then, a substrate solution containing tert-butyl 3-carbonyl-5-hexenoate was pumped from a container 1 to the tubular microchannel reactor 3 using the feeding pump 2. The back pressure of the back pressure regulator 4 was set at 0.5 MPa, and the temperature in the tubular microchannel reactor 3 was controlled at 30° C. The flow rate of the feeding pump 2 was adjusted such that the residence time of the substrate solution in the tubular microchannel reactor 3 was 8 min. The reaction mixture flowing out of the micro reaction system was collected into a collecting bottle 5 and subsequently subjected to extraction with ethyl acetate 3 times. The organic phases were combined, washed with water and saturated brine solution, and subsequently dried with anhydrous sodium sulfate and concentrated under vacuum to obtain a target product tert-butyl (R)-3-hydroxy-5-hexenoate (96.8% yield and 99.7% ee).

The substrate solution provided herein contained a disodium hydrogen phosphate-potassium dihydrogen phosphate buffered solution (pH 7) as solvent, 20 g/L of tert-butyl 3-carbonyl-5-hexenoate, 15 g/L of isopropanol, 0.0125 g/L of NADP$^+$ and 100 g/L of dimethyl sulfoxide. The continuous enzymatic asymmetric carbonyl reduction reaction was enabled when the substrate solution flowing through the tubular microchannel reactor 3 that was filled with the carbonyl reductase/isopropanol dehydrogenase co-immobilized catalyst 31.

Example 3 Preparation of Target Product tert-butyl (R)-3-hydroxy-5-hexenoate

The micro reaction system shown in FIG. 1 was adopted herein, where the microchannel reactor 3 was a tubular microchannel reactor. 2.5 g of the carbonyl reductase/isopropanol dehydrogenase co-supported catalyst prepared in Example 1 was filled into the tubular microchannel reactor 3 with an inner diameter of 5 mm and a length of 200 mm. A disodium hydrogen phosphate-potassium dihydrogen phosphate buffered solution (pH 7.0) was first pumped into the tubular microchannel reactor 3 at a flow rate of 5 mL/min using a feeding pump 2 to wash the carbonyl reductase/isopropanol dehydrogenase co-supported catalyst 31 for 5 min. Then, a substrate solution containing tert-butyl 3-carbonyl-5-hexenoate was pumped from a container 1 to the tubular microchannel reactor 3 using the feeding pump 2. The back pressure of the back pressure regulator 4 was set at 0.5 MPa, and the temperature in the tubular microchannel reactor 3 was controlled at 30° C. The flow rate of the feeding pump 2 was adjusted such that the residence time of the substrate solution in the tubular microchannel reactor 3 was 8 min. The reaction mixture flowing out of the micro reaction system was collected into a collecting bottle 5 and subsequently subjected to extraction with ethyl acetate 3 times. The organic phases were combined, washed with water and saturated brine, and subsequently dried with anhydrous sodium sulfate and concentrated under vacuum to obtain a target product tert-butyl (R)-3-hydroxy-5-hexenoate (97.8% yield, and 99.8% ee).

The substrate solution provided herein contained a disodium hydrogen phosphate-potassium dihydrogen phosphate buffered solution (pH 7) as solvent, 20 g/L of tert-butyl 3-carbonyl-5-hexenoate, 15 g/L of isopropanol, 0.0125 g/L of NADP$^+$ and 100 g/L of dimethyl sulfoxide. The continuous enzymatic asymmetric carbonyl reduction reaction was enabled when the substrate solution flowing through the tubular microchannel reactor 3 that was filled with the carbonyl reductase/isopropanol dehydrogenase co-immobilized catalyst 31.

Example 4 Preparation of Target Product tert-butyl (R)-3-hydroxy-5-hexenoate The micro reaction system shown in FIG. 1 was adopted herein, where the microchannel reactor 3 was a tubular microchannel reactor. 1.25 g of the carbonyl reductase/isopropanol dehydrogenase co-supported catalyst prepared in Example 1 was filled into the tubular microchannel reactor 3 with an inner diameter of 2.5 mm and a length of 200 mm. A disodium hydrogen phosphate-potassium dihydrogen phosphate buffered solution (pH 7.0) was first pumped into the tubular microchannel reactor 3 at a flow rate of 5 mL/min using a feeding pump 2 to wash the carbonyl reductase/isopropanol dehydrogenase co-supported catalyst 31 for 5 min. Then, a substrate solution containing tert-butyl 3-carbonyl-5-hexenoate was pumped from a container 1 to the tubular microchannel reactor 3 using the feeding pump 2. The back pressure of the back pressure regulator 4 was set at 0.5 MPa, and the temperature in the tubular microchannel reactor 3 was controlled at 30° C. The flow rate of the feeding pump 2 was adjusted such that the residence time of the substrate solution in the tubular microchannel reactor 3 was 8 min. The reaction mixture flowing out of the micro reaction system was collected into a collecting bottle 5 and subsequently subjected to extraction with ethyl acetate for 3 times. The organic phases were combined, washed with water and saturated brine, and subsequently dried with anhydrous sodium sulfate and concentrated under vacuum to obtain a target product tert-butyl (R)-3-hydroxy-5-hexenoate (98.8% yield and 99.8% ee).

The substrate solution provided herein contained a disodium hydrogen phosphate-potassium dihydrogen phosphate buffered solution (pH 7) as solvent, 20 g/L of tert-butyl 3-carbonyl-5-hexenoate, 15 g/L of isopropanol, 0.0125 g/L of NADP$^+$ and 100 g/L of dimethyl sulfoxide. The continuous enzymatic asymmetric carbonyl reduction reaction was enabled when the substrate solution flowing through the tubular microchannel reactor 3 that was filled with the carbonyl reductase/isopropanol dehydrogenase co-immobilized catalyst 31.

Figure 2:
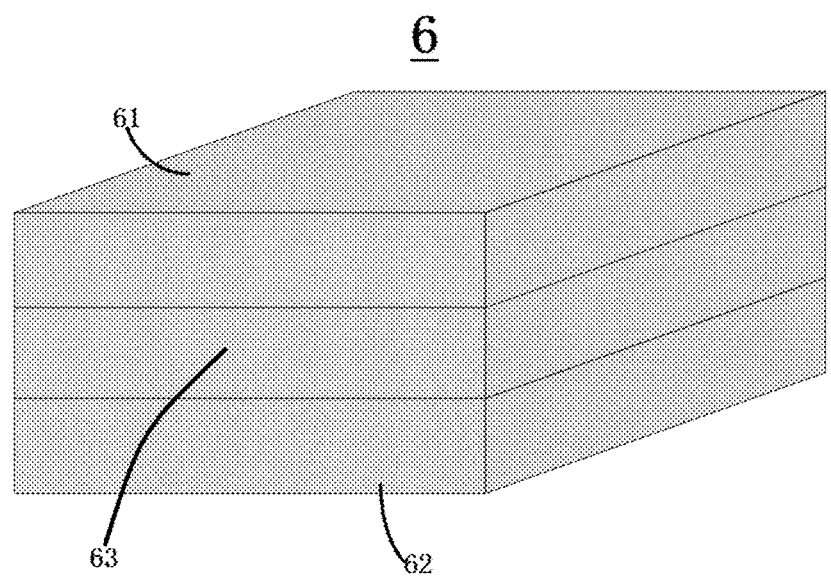
FIG. 2 is a schematic diagram of a plate-type microchannel reactor in accordance with an embodiment of this disclosure.

Example 5 Preparation of Target Product tert-butyl (R)-3-hydroxy-5-hexenoate The micro reaction system shown in FIG. 1 was adopted herein, where the microchannel reactor 3 was a plate-type microchannel reactor 6 shown in FIG. 2. The carbonyl reductase/isopropanol dehydrogenase co-supported catalyst prepared in Example 1 was filled in a reaction fluid channel of the plate-type microchannel reactor 3 made of 316 L stainless steel, where the reaction fluid channel had a cross section of 400 μm (width)×600 μm (height), a hydraulic diameter of 480 μm, and a length of 100 mm. As shown in FIG. 2, the plate-type microchannel reactor 6 had a cuboid structure with a length of 12 cm, a width of 10 cm and a height of 3 cm, and included a first temperature control layer 61, a reaction layer 63 and a second temperature control layer 62 from top to bottom. The first temperature control layer 61 and the second temperature control layer 62 were configured to adjust the temperature of the reaction layer 63, and the reaction fluid channel was arranged in the reaction layer 63.

A disodium hydrogen phosphate-potassium dihydrogen phosphate buffered solution (pH 7.0) was first pumped into the plate-type microchannel reactor 3 at a flow rate of 5 m/min to wash the co-supported catalyst for 5 min. Then, a substrate solution containing tert-butyl 3-carbonyl-5-hexenoate was pumped from a container 1 to the plate-type microchannel reactor 3 using a feeding pump 2. The back pressure of the back pressure regulator 4 was set at 0.5 MPa, and the temperature in the plate-type microchannel reactor 3 was controlled at 30° C. The flow rate of the feeding pump 2 was adjusted such that the residence time of the substrate solution in the tubular microchannel reactor 3 was 8 min. The reaction mixture flowing out of the micro reaction system was collected into a collecting bottle 5 and subsequently subjected to extraction with ethyl acetate for 3 times. The organic phases were combined, washed with water and saturated brine, and subsequently dried with anhydrous sodium sulfate and concentrated under vacuum to obtain a target product tert-butyl (R)-3-hydroxy-5-hexenoate (99.8% yield and 99.9% ee).

The substrate solution provided herein contained a disodium hydrogen phosphate-potassium dihydrogen phosphate buffered solution (pH 7) as solvent, 20 g/L of tert-butyl 3-carbonyl-5-hexenoate, 15 g/L of isopropanol, 0.0125 g/L of NADP$^+$ and 100 g/L of dimethyl sulfoxide. The continuous enzymatic asymmetric carbonyl reduction reaction was enabled when the substrate solution flowing through the plate-type microchannel reactor 3, whose reaction fluid channel was filled with the carbonyl reductase/isopropanol dehydrogenase co-immobilized catalyst 31.

Example 6 Preparation of Target Product tert-butyl (R)-3-hydroxy-5-hexenoate The preparation of tert-butyl (R)-3-hydroxy-5-hexenoate in this example was basically the same as that in the Example 2 except that the phosphate buffered solution used herein was a disodium hydrogen phosphate-sodium dihydrogen phosphate buffered solution with a pH of 7.0. In this example, the target product tert-butyl (R)-3-hydroxy-5-hexenoate had 96.8% yield and 99.7% ee.

Example 7 Preparation of Target Product tert-butyl (R)-3-hydroxy-5-hexenoate The preparation of tert-butyl (R)-3-hydroxy-5-hexenoate in this example was basically the same as that in the Example 2 except that the substrate solution used herein employed sulfolane (100 g/L) as the organic solvent. In this example, the target product tert-butyl (R)-3-hydroxy-5-hexenoate had 96.5% yield and 99.6% ee.

Example 8 Preparation of Target Product tert-butyl (R)-3-hydroxy-5-hexenoate The preparation of tert-butyl (R)-3-hydroxy-5-hexenoate in this example was basically the same as that in the Example 2 except that the substrate solution used herein employed N-methylpyrrolidone (100 g/L) as the organic solvent. In this example, the target product tert-butyl (R)-3-hydroxy-5-hexenoate had 96.4% yield and 99.5% ee.

Example 9 Preparation of Target Product tert-butyl (R)-3-hydroxy-5-hexenoate The preparation of tert-butyl (R)-3-hydroxy-5-hexenoate in this example was basically the same as that in the Example 2 except that the substrate solution used herein employed N, N-dimethylformamide (100 g/L) as the organic solvent. In this example, the target product tert-butyl (R)-3-hydroxy-5-hexenoate had 96.5% yield and 99.6% ee.

Example 10 Preparation of Target Product tert-butyl (R)-3-hydroxy-5-hexenoate The preparation of tert-butyl (R)-3-hydroxy-5-hexenoate in this example was basically the same as that in the Example 2 except that the substrate solution used herein employed acetone (100 g/L) as the organic solvent. In this example, the target product tert-butyl (R)-3-hydroxy-5-hexenoate had 96.4% yield and 99.2% ee.

Example 11 Preparation of Target Product tert-butyl (R)-3-hydroxy-5-hexenoate The preparation of tert-butyl (R)-3-hydroxy-5-hexenoate in this example was basically the same as that in the Example 2 except that the substrate solution used herein employed acetonitrile (100 g/L) as the organic solvent. In this example, the target product tert-butyl (R)-3-hydroxy-5-hexenoate had 96.3% yield and 99.1% ee.

Example 12 Preparation of Target Product tert-butyl (R)-3-hydroxy-5-hexenoate The preparation of tert-butyl (R)-3-hydroxy-5-hexenoate in this example was basically the same as that in the Example 2 except that the temperature of the tubular microchannel reactor 3 used herein was controlled at 20° C. In this example, the target product tert-butyl (R)-3-hydroxy-5-hexenoate had 96.6% yield and 99.7% ee.

Example 13 Preparation of Target Product tert-butyl (R)-3-hydroxy-5-hexenoate The preparation of tert-butyl (R)-3-hydroxy-5-hexenoate in this example was basically the same as that in the Example 2 except that the temperature of the tubular microchannel reactor 3 used herein was controlled at 25° C. In this example, the target product tert-butyl (R)-3-hydroxy-5-hexenoate had 96.7% yield and 99.8% ee.

Example 14 Preparation of Target Product tert-butyl (R)-3-hydroxy-5-hexenoate The preparation of tert-butyl (R)-3-hydroxy-5-hexenoate in this example was basically the same as that in the Example 2 except that the temperature of the tubular microchannel reactor 3 used herein was controlled at 35° C. In this example, the target product tert-butyl (R)-3-hydroxy-5-hexenoate had 96.5% yield and 99.5% ee.

Example 15 Preparation of Target Product tert-butyl (R)-3-hydroxy-5-hexenoate The preparation of tert-butyl (R)-3-hydroxy-5-hexenoate in this example was basically the same as that in the Example 2 except that the temperature of the tubular microchannel reactor 3 used herein was controlled at 40° C. In this example, the target product tert-butyl (R)-3-hydroxy-5-hexenoate had 95% yield and 98.7% ee.

Example 16 Preparation of Target Product tert-butyl (R)-3-hydroxy-5-hexenoate The preparation of tert-butyl (R)-3-hydroxy-5-hexenoate in this example was basically the same as that in the Example 2 except that the residence time of the substrate solution in the tubular microchannel reactor 3 was 30 min in this example. The target product tert-butyl (R)-3-hydroxy-5-hexenoate had 97.9% yield and 99.8% ee.

Example 17 Preparation of Target Product tert-butyl (R)-3-hydroxy-5-hexenoate The preparation of tert-butyl (R)-3-hydroxy-5-hexenoate in this example was basically the same as that in the Example 2 except that the residence time of the substrate solution in the tubular microchannel reactor 3 was 3 min in this example. The target product tert-butyl (R)-3-hydroxy-5-hexenoate had 93.1% yield and 99.2% ee.

Example 18 Preparation of Target Product tert-butyl (R)-3-hydroxy-5-hexenoate The preparation of tert-butyl (R)-3-hydroxy-5-hexenoate in this example was basically the same as that in the Example 2 except that the back pressure of the back pressure regulator 4 used herein was 0.1 MPa. The target product tert-butyl (R)-3-hydroxy-5-hexenoate had 96.6% yield and 99.5% ee.

Example 19 Preparation of Target Product tert-butyl (R)-3-hydroxy-5-hexenoate The preparation of tert-butyl (R)-3-hydroxy-5-hexenoate in this example was basically the same as that in the Example 2 except that the back pressure of the back pressure regulator 4 used herein was 2 MPa. The target product tert-butyl (R)-3-hydroxy-5-hexenoate had 97.2% yield and 99.6% ee.

Example 20 Preparation of Target Product tert-butyl (R)-3-hydroxy-5-hexenoate The preparation of tert-butyl (R)-3-hydroxy-5-hexenoate in this example was basically the same as that in the Example 2 except that the back pressure of the back pressure regulator 4 used herein was 3 MPa. The target product tert-butyl (R)-3-hydroxy-5-hexenoate had 97.5% yield and 99.8% ee.

Example 21 Preparation of target product methyl (R)-3-hydroxy-5-hexenoate

The preparation in this example was basically the same as that in the Example 2 except that the substrate used herein was methyl 3-carbonyl-5-hexenoate. The target product methyl (R)-3-hydroxy-5-hexenoate had 96.5% yield and 99.8% ee.

Example 22 Preparation of target product ethyl (R)-3-hydroxy-5-hexenoate

The preparation in this example was basically the same as that in the Example 2 except that the substrate used herein was ethyl 3-carbonyl-5-hexenoate. The target product ethyl (R)-3-hydroxy-5-hexenoate had 96.7% yield and 99.7% ee.

Example 23 Preparation of Target Product tert-butyl (R)-3-hydroxy-5-hexenoate The preparation of tert-butyl (R)-3-hydroxy-5-hexenoate in this example was basically the same as that in the Example 2 except that the concentration of tert-butyl 3-carbonyl-5-hexenoate in the substrate solution used herein was 40 g/L. The target product tert-butyl (R)-3-hydroxy-5-hexenoate had 95.1% yield and 99.6% ee.

Example 24 Preparation of Target Product tert-butyl (R)-3-hydroxy-5-hexenoate The preparation of tert-butyl (R)-3-hydroxy-5-hexenoate in this example was basically the same as that in the Example 2 except that the microchannel reactor was further sequentially connected to a microfluidic liquid-liquid extractor and a liquid-liquid membrane separator to achieve continuous enzymatic reaction, liquid-liquid extraction and separation. The target product tert-butyl (R)-3-hydroxy-5-hexenoate had 98.8% yield and 99.8% ee.

Example 25 Preparation of Target Product tert-butyl (R)-3-hydroxy-5-hexenoate The preparation of tert-butyl (R)-3-hydroxy-5-hexenoate in this example was basically the same as that in the Example 2 except that the microchannel reactor was further connected to a two-stage extraction and separation unit to achieve continuous enzymatic reaction, liquid-liquid extraction and separation. The two-stage extraction and separation unit was composed of a first microfluidic liquid-liquid extractor, a first liquid-liquid membrane separator, a second microfluidic liquid-liquid extractor and a second liquid-liquid membrane separator that were sequentially connected in series. The target product tert-butyl (R)-3-hydroxy-5-hexenoate had 98.9% yield and 99.8% ee.

Example 26 Preparation of Target Product tert-butyl (R)-3-hydroxy-5-hexenoate The preparation of tert-butyl (R)-3-hydroxy-5-hexenoate in this example was basically the same as that in the Example 2 except that the microchannel reactor was further connected to a three-stage extraction and separation unit to achieve continuous enzymatic reaction, liquid-liquid extraction and separation. The three-stage extraction and separation unit was composed of a first microfluidic liquid-liquid extractor, a first liquid-liquid membrane separator, a second microfluidic liquid-liquid extractor, a second liquid-liquid membrane separator, a third microfluidic liquid-liquid extractor, a third liquid-liquid membrane separator that were sequentially connected in series. The target product tert-butyl (R)-3-hydroxy-5-hexenoate had 99.2% yield and 99.9% ee.

Example 27 Preparation of Target Product tert-butyl (R)-3-hydroxy-5-hexenoate The preparation of tert-butyl (R)-3-hydroxy-5-hexenoate in this example was basically the same as that in the Example 2 except that the microchannel reactor was further connected to a centrifugal extractor to achieve continuous enzymatic reaction, liquid-liquid extraction and separation. The target product tert-butyl (R)-3-hydroxy-5-hexenoate had 99.2% yield and 99.8% ee.

Example 28 Preparation of Target Product tert-butyl (R)-3-hydroxy-5-hexenoate The preparation of tert-butyl (R)-3-hydroxy-5-hexenoate in this example was basically the same as that in the Example 2 except that the microchannel reactor was further connected to two centrifugal extractors installed in series to achieve continuous enzymatic reaction, liquid-liquid extraction and separation. The target product tert-butyl (R)-3-hydroxy-5-hexenoate had 99.6% yield and 99.9% ee.

Example 29 Preparation of Target Product tert-butyl (R)-3-hydroxy-5-hexenoate The preparation of tert-butyl (R)-3-hydroxy-5-hexenoate in this example was basically the same as that in the Example 2 except that the microchannel reactor was further connected to three centrifugal extractors installed in series to achieve continuous enzymatic reaction, liquid-liquid extraction and separation. The target product tert-butyl (R)-3-hydroxy-5-hexenoate had 99.8% yield and 99.9% ee.

Comparative Example 1 Preparation of Target Product tert-butyl (R)-3-hydroxy-5-hexenoate In this example, a batch reactor was used to prepare tert-butyl (R)-3-hydroxy-5-hexenoate, and the specific preparation method was shown as follows.

5 g of the carbonyl reductase/isopropanol dehydrogenase co-immobilized catalyst prepared in Example 1 was placed in the batch reactor, to which the substrate tert-butyl 3-carbonyl-5-hexenoate (0.8 g), isopropanol (0.6 g), $NADP^+$ (0.8 mg), dimethyl sulfoxide (4 g) and a disodium hydrogen phosphate-potassium dihydrogen phosphate buffered solution (pH 7.0, 35 mL) were added. Then the batch reactor was shaken at 30° C. and 200 rpm in a thermostatic shaker for reaction, and during the reaction, the reaction mixture was regularly sampled for analysis. The results showed that the substrate tert-butyl 3-carbonyl-5-hexenoate reached a conversion of about 35% after 1 h; about 52% after 2 h; about 64% after 3 h; and about 97% after 12 h. After 12 h, the target product tert-butyl (R)-3-hydroxy-5-hexenoate had a yield of 88%.

The Comparative Example 1 was the same as Examples 1-5 in terms of the initial ratio of the reactants. Compared to the traditional batch reactor, the micro-reaction system based continuous flow method used herein led to very short reaction time, less side reactions and much improved yield of the target product (R)-3-hydroxy-5-hexenoate. In addition, the continuous-flow process can eliminate the need for manual workup procedures including filtration, liquid-liquid extraction and separation, simplifying the operation and achieving continuous preparation and high space and time efficiency, thereby reducing the processing time needed, minimizing the energy consumed and the waste generated.

It should be noted that the embodiments provided herein are merely illustrative, and are not intended to limit the invention. Any changes, modifications and replacements made by those skilled in the art without departing from the spirit of the invention should fall within the scope of the invention defined by the appended claims.

What is claimed is:

1. A continuous-flow method for preparing (R)-3-hydroxy-5-hexenoate of formula (I) using a micro reaction system, the micro reaction system comprising a microchannel reactor,

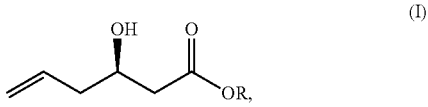
(I)

the method comprising:
(1) co-immobilizing a carbonyl reductase and an isopropanol dehydrogenase onto an inert solid medium to prepare a carbonyl reductase/isopropanol dehydrogenase co-immobilized catalyst; and filling the microchannel reactor with the co-immobilized catalyst;
(2) pumping a substrate solution containing 3-carbonyl-5-hexenoate of formula (II) into the microchannel reactor filled with the carbonyl reductase/isopropanol dehydrogenase co-immobilized catalyst prepared in step (1) to perform an asymmetric carbonyl reduction reaction; and

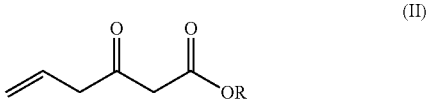
(II)

(3) collecting the reaction mixture flowing out of the microchannel reactor followed by separation and purification to obtain a target product (R)-3-hydroxy-5-hexenoate;

wherein R is linear or branched $C_1$-$C_8$ alkyl group, linear or branched $C_3$-$C_8$ cycloalkyl group, monosubstituted or polysubstituted aryl group, or monosubstituted or polysubstituted aralkyl group;

wherein an amino acid sequence of the carbonyl reductase is SEQ ID NO: 1; an amino acid sequence of the isopropanol dehydrogenase is SEQ ID NO: 2; and wherein the yield of the product (R)-3-hydroxy-5-hexenoate is increased from 80% to more than 95% compared to a method using a batch reactor.

2. The method of claim 1, wherein in step (1), the inert solid medium is a composite material of polyvinyl alcohol and polyethylene glycol; and the step of co-immobilizing a carbonyl reductase and an isopropanol dehydrogenase onto an inert solid medium to prepare the co-immobilized catalyst comprises:
(a) preparing an aqueous solution of the polyvinyl alcohol and the polyethylene glycol; heating the aqueous solution until the aqueous solution becomes clear; and cooling the aqueous solution to 50° C. or less to obtain a first solution;
(b) adding a crude carbonyl reductase solution and a crude isopropanol dehydrogenase solution into the first solution followed by uniform mixing to obtain a second solution; and
(c) dropwise adding the second solution onto a polyethylene film; drying the polyethylene film at 35-40° C. for 0.5-1 hour to obtain the co-immobilized catalyst; and storing the co-immobilized catalyst at 4° C. for later use;

wherein a weight ratio of the polyvinyl alcohol to the polyethylene glycol is 5:1-3;

the crude carbonyl reductase solution and the crude isopropanol dehydrogenase solution both have an initial concentration of 10%-30% (w/v); and in step (b), a volume ratio of the crude carbonyl reductase solution to the crude isopropanol dehydrogenase solution to the first solution in the second solution is 2:1:5-10.

3. The method of claim 1, wherein the microchannel reactor is a tubular microchannel reactor or a plate-type microchannel reactor.

4. The method of claim 3, wherein the microchannel reactor is a tubular microchannel reactor with an inner diameter of 100 μm-20 mm; or wherein the microchannel reactor is a plate-type microchannel reactor having a reaction fluid channel with a hydraulic diameter of 100 μm-20 mm.

5. The method of claim 1, wherein in step (2), the substrate solution is prepared by dissolving 3-carbonyl-5-hexenoate (II), isopropanol, coenzyme $NADP^+$ and an organic solvent into a phosphate buffered solution (PBS); and the organic solvent is a polar aprotic solvent selected from the group consisting of N,N-dimethylformamide, dimethyl sulfoxide, N-methylpyrrolidone, sulfolane, 1,3-dimethyl-2-imidazolinone, hexamethylphosphoric triamide, acetonitrile and a ketone solvent.

6. The method of claim 5, wherein the substrate solution comprises 1-100 g/L of 3-carbonyl-5-hexenoate (II), 1-50 g/L of isopropanol, 0.005-0.1 g/L of the coenzyme $NADP^+$ and 20-250 g/L of the organic solvent.

7. The method of claim 5, wherein the phosphate buffered solution is an aqueous solution of a mixture of disodium hydrogen phosphate and sodium dihydrogen phosphate or potassium dihydrogen phosphate; and the phosphate buffered solution has a pH of 6-8.

8. The method of claim 1, wherein in step (2), the asymmetric carbonyl reduction reaction is performed at 15-40° C.; and a residence time of the substrate solution in the microchannel reactor is 0.1-30 min.

9. The method of claim 1, wherein the micro reaction system further comprises a feeding pump and a back pressure regulator; an inlet of the microchannel reactor is connected to the feeding pump, and an outlet of the microchannel reactor is connected to the back pressure regulator; and a back pressure range of the back pressure regulator is 0.1-3 MPa.

10. The method of claim 9, wherein the microchannel reactor is further sequentially connected to a microfluidic liquid-liquid extractor and a liquid-liquid membrane separator to achieve continuous enzymatic reaction, liquid-liquid extraction and separation.

11. The method of claim 9, wherein the microchannel reactor is further connected to a multi-stage extraction and separation unit to achieve continuous enzymatic reaction, liquid-liquid extraction and separation; and the multi-stage extraction and separation unit is composed of at least two pairs of microfluidic liquid-liquid extractor and liquid-liquid membrane separator that are sequentially connected in series.

12. The method of claim 9, wherein the microchannel reactor is further connected to a centrifugal extractor or at least two centrifugal extractors installed in series to achieve continuous enzymatic reaction, liquid-liquid extraction and separation.

* * * * *